United States Patent [19]

Mondet et al.

[11] Patent Number: 5,660,820
[45] Date of Patent: Aug. 26, 1997

[54] HAIR-SETTING COMPOSITION

[75] Inventors: Jean Mondet, Drancy; Jean-Michel Sturla, Suresnes; Bertrand Lion, Livry Gargan; Christine Dupuis; Colette Cazeneuve, both of Paris, all of France

[73] Assignee: L'Oreal, Paris, France

[21] Appl. No.: 483,266

[22] Filed: Jun. 7, 1995

Related U.S. Application Data

[62] Division of Ser. No. 256,019, filed as PCT/FR93/01630, Oct. 28, 1993, abandoned.

[30] Foreign Application Priority Data

Oct. 28, 1992 [FR] France .................. 92 12872

[51] Int. Cl.$^6$ ........................................ A61K 7/11
[52] U.S. Cl. .............. 424/70.16; 424/70.1; 424/70.11; 424/47
[58] Field of Search ................ 424/70.1, 70.11, 424/70.16, 47

[56] References Cited

U.S. PATENT DOCUMENTS 4,960,814  10/1990  Wu et al. .................. 524/312

FOREIGN PATENT DOCUMENTS

| 0418676 | 3/1991 | European Pat. Off. . |
| 2439798 | 5/1980 | France . |
| 4-103509 | 4/1992 | Japan . |

*Primary Examiner*—Jyothsan Venkat
*Attorney, Agent, or Firm*—Oliff & Berridge

[57] ABSTRACT

An aqueous cosmetic composition for fixing hair is an aqueous particulate dispersion. The dispersion includes particles of a film-forming polymer containing carboxylic acid functions neutralized to a degree of neutralization from between 10 and 80 percent using a non-volatile monobasic agent. The particles have an average diameter of between 10 and 300 nm. The aqueous dispersion also includes at least one plasticizing agent. The composition may be used as an aerosol lacquer, a fixing or setting lotion or a styling mousse.

7 Claims, No Drawings

HAIR-SETTING COMPOSITION

This is a division of application Ser. No. 08/256,019, filed Aug. 29, 1994, now abandoned, which in turn is a national stage application of PCT/FR/93/01063, filed Oct. 28, 1993.

FIELD OF THE INVENTION

The present invention relates to an aqueous cosmetic composition for fixing the hair, containing an aqueous dispersion of particles of a film-forming polymer and of at least one plasticizing agent.

BACKGROUND

More especially, the present invention relates to hair-care compositions in the form of an aerosol lacquer, a fixing or setting lotion or alternatively a styling mousse.

For some years, the production of aqueous cosmetic hair-care compositions has aroused very special interest. In effect, the use of alcohol such as ethanol or isopropanol, alone or mixed with a small proportion of water, can have some drawbacks, in particular an increase in inflammability when the composition is in the form of an aerosol lacquer.

Moreover, on ecological grounds, with a view to preserving, in particular, the ozone layer, the present tendency is to replace fluorochlorohydrocarbons of the "FREON" type in aerosols by less toxic propellants such as hydrocarbons, compressed air or dimethyl ether.

These various requirements regarding the nature of the vehicle and of the propellent agent are extremely difficult to reconcile on account of the many factors involved.

Thus, while most water-soluble film-forming polymers can, in solution in water, where appropriate in the presence of a plasticizing agent, lead to the production of an aerosol lacquer in the presence of an inert propellent agent such as dimethyl ether, such a lacquer suffers, however, from two major drawbacks.

The first is the low power of fixing the hair, inasmuch as only a low concentration of film-forming resin (<10%) can be employed.

In effect, an increase in the concentration results in an increase in viscosity, and the outcome is that good diffusion can no longer be obtained.

The second drawback is the drying time, which is especially long in comparison to hair-care compositions in aqueous-alcoholic or alcoholic solution, this being due to the fact that the vehicle is chiefly water and that, the greater its proportion, the longer it will take to dry.

SUMMARY OF THE INVENTION

An aqueous cosmetic composition for fixing hair comprises an aqueous particulate dispersion. The dispersion comprises particles of a film-forming polymer containing carboxylic acid functions neutralized to a degree of neutralization from between 10 and 80 percent using a non-volatile monobasic agent. The particles have an average diameter of between 10 and 300 nm. The aqueous dispersion also comprises at least one plasticizing agent. The composition may be used as an aerosol lacquer, a fixing or setting lotion or a styling mousse.

DESCRIPTION OF PREFERRED EMBODIMENTS

After many studies on a very large number of film-forming polymers for hair-care use, it has just now been found possible to overcome these drawbacks, and thus to obtain excellent aqueous cosmetic compositions for fixing the hair using an aqueous dispersion of particles of a film-forming polymer and at least one plasticizing agent.

Aqueous dispersions of particles of a film-forming polymer are generally designated by the terms "latex" or "pseudolatex".

However, the term "pseudolatex" denotes a dispersion consisting of generally spherical particles of a film-forming polymer, these being obtained by dispersion of the polymer in a suitable aqueous phase.

This term should not be confused with the term "latex" or "synthetic latex", which is also a dispersion consisting of particles of a polymer which are obtained directly by polymerization of one or more monomers in a suitable aqueous phase.

According to the invention, the aqueous dispersion of particles of film-forming polymer is of the "pseudolatex" type, and in so far as it contains a plasticizing agent, it will be designated hereinafter by the term "plasticized pseudolatex".

The use of a plasticized pseudolatex enables cosmetic compositions for fixing the hair to be endowed with a very large number of advantages, and especially:

1. a much faster drying time, this being due to the fact that less water can be used while having a high concentration of film-forming polymer without viscosity problems being encountered, the polymer being dispersed in the aqueous phase and not dissolved, 2. the possibility of using a large quantity of propellent agent such as dimethyl ether in aerosol lacquers, with which propellent agent no segregation of constituents has been observed with quantities larger than 35% by weight, thereby also favouring a better drying time, 3. the production of excellent cosmetic properties relating to fixing power, disentangling, the feel of the hair and the absence of powdering, 4. good removal on shampooing without the need to use a specific shampoo, 5. absence of a whitish appearance of the hair before drying, in particular when the propellent agent of the aerosol lacquers is dimethyl ether, this being due to the fact that the particle size is very small.

The subject of the present invention, as a new industrial product, is an aqueous cosmetic composition for fixing the hair, this consisting of an aqueous dispersion of:

a) particles of a film-forming polymer containing carboxylic acid functions, having an average diameter of between 10 and 300 nm, the said polymer being chosen from:

(i) vinyl acetate/crotonic acid polyoxyethylenated copolymers, (ii) vinyl acetate/crotonic acid copolymers, (iii) vinyl acetate/crotonic acid/vinyl neodecanoate terpolymers, (iv) N-octylacrylamide/methyl methacrylate/hydroxypropyl methacrylate/acrylic acid/tert-butylaminoethyl methacrylate copolymers, (v) methyl vinyl ether/maleic anhydride alternating copolymers monoesterified with butanol, (vi) acrylic acid/ethyl acrylate/N-tert-butyl-acrylamide terpolymers, and (vii) polymers corresponding to the following general formula:

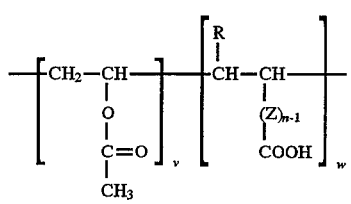

(I)

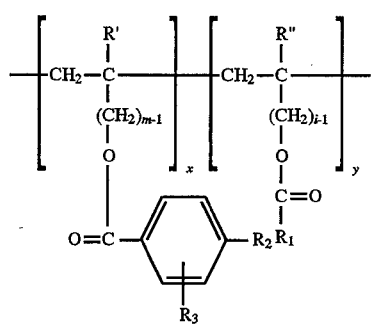

in which:

R, R' and R", which may be identical or different, represent a hydrogen atom or a methyl radical, m, n and t are 1 or 2, $R_1$ represents a saturated or unsaturated, linear or branched alkyl radical having from 2 to 21 carbon atoms, $R_2$ represents a hydrogen atom or a methyl, ethyl, tert-butyl, ethoxy, butoxy or dodecyloxy radical, $R_3$ represents a hydrogen atom, an alkyl radical having 1 to 4 carbon atoms or an alkoxy radical having 1 to 4 carbon atoms, Z represents a bivalent radical selected from the group consisting of: —$CH_2$—, —$CH_2$—O—$CH_2$—and—$CH_2$—O—$(CH_2)_2$—, v represents from 10 to 91% and preferably from 36 to 84% by weight, w represents from 3 to 20% and preferably from 6 to 12% by weight, x represents from 4 to 60% and preferably from 6 to 40% by weight, and y represents from 0 to 40% and preferably from 4 to 30% by weight, v+w+x+y being equal to 100%, and the carboxylic acid functions of the said polymer being neutralized to a degree of neutralization of between 10 and 80% using a non-volatile monobasic agent, and b) at least one plasticizing agent, the said agent being distributed according to its partition coefficient between the said particles and the aqueous phase.

Among vinyl acetate/crotonic acid polyoxyethylenated copolymers, "Aristoflex A" of acid value 56 of the company Hoechst may be mentioned in particular.

As vinyl acetate/crotonic acid copolymers, "Luviset CA66" of acid value 65 (vinyl acetate/crotonic acid 90:10) of the company BASF may be mentioned.

Among vinyl acetate/crotonic acid/vinyl neodecanoate terpolymers, "Resin 28-29-30" of acid value 65 of the company National Starch may be mentioned.

As N-octylacrylamide/methyl methacrylate/hydroxypropyl methacrylate/acrylic acid/tert-butylaminoethyl methacrylate copolymers, "Amphomer" of acid value 137 of the company National Starch may be mentioned.

Among methyl vinyl ether/maleic anhydride alternating copolymers monoesterified with butanol, "Gantrez ES425" of acid value 260 (methyl vinyl ether/maleic anhydride 50:50) of the company GAF may be mentioned.

As acrylic acid/ethyl acrylate/N-tert-butylacrylamide terpolymers, special mention may be made of "Ultrahold 8" of acid value 62 of the company BASF.

As copolymers of formula (I), those described in French Patent No. 78/30,596 (2,439,798) may be mentioned, and especially the following copolymers:

vinyl acetate/crotonic acid/vinyl 4-tert-butylbenzoate 65:10:25, vinyl acetate/crotonic acid/vinyl 4-tert-butyl-benzoate/vinyl neodecanoate 57:10:25:8, vinyl acetate/crotonic acid/vinyl 4-tert-butylbenzoate/vinyl neodecanoate 70:10:10:10, vinyl acetate/crotonic acid/vinyl benzoate/vinyl neodecanoate 70:10:10:10, vinyl acetate/crotonic acid/vinyl 4-tert-butyl-benzoate/allyl stearate 70:10:10:10.

According to the invention, it is desirable for the said aqueous dispersion to lead after drying to the formation of a film whose surface energy is between 30 and 55 mJ/m$^2$ and whose polarity is between 0 and 0.34 and preferably less than 0.25.

The surface energy of the film is determined by depositing a drop of water and a drop of diiodomethane on the film, measuring the angle formed by each drop with the film and then calculating the surface energy of the said film according to the method described in "Wettability of Some Low Energy Surfaces", A. EL. Shimi, E. D. Goddard—Journal of Colloid and Interface Science, Vol. 48, no. 2 (1974).

The polarity of the film is calculated according to the method described in "Polar and Nonpolar Interactions in Adhesion" S. Wu, J. Adhesion, vol.5, pp 39–55, (1973).

The film-forming polymers containing carboxylic acid functions as defined above are synthetic polymers preferably having an average molecular weight of between 5,000 and 700,000, measured, for example, in steric exclusion chromatography.

These polymers are insoluble in water and are, for the most part, film-forming polymers commonly used for the production of cosmetic compositions for fixing the hair.

The pseudolatices or aqueous dispersions of particles of film-forming polymer of the cosmetic compositions according to the invention are obtained according to known methods for preparing pseudolatices, subject, however, to certain special features which will be mentioned below.

The general process for preparing pseudolatices consists in dissolving a water-insoluble polymer in an organic solvent which is soluble or partially soluble in water, in dispersing the solution thereby obtained in water with stirring and in thereafter removing the organic solvent by evaporation under vacuum, which results in a suspension consisting of particles of the polymer whose size is generally less than 1 μm.

According to this general process, the use of a surfactant, a mixture of surfactants or a protective colloidal polymer, or alternatively of a surfactant/protective colloidal polymer mixture, is essential for the purpose of obtaining good stabilization of the particles.

The film-forming polymers containing carboxylic acid functions as defined above cannot be used as they are in the preparation of the pseudolatices, but must be neutralized to a degree of neutralization of less than 100% for the purpose of avoiding their complete solubilization in water.

By partial neutralization of the polymers, it was found to be possible to obtain pseudolatices which are especially stable in the absence of a hydrophilic stabilizer or a surfactant or alternatively of a protective colloid.

The degree of neutralization of the film-forming polymers containing carboxylic acid functions must hence be fully determined in such a way that they remain insoluble in water while being soluble in the organic solvent.

It is self-evident that the upper limiting degree of neutralization which should not be exceeded in order for the polymer to remain insoluble in water will be dependent on the nature of each film-forming polymer containing carboxylic acid functions. In general, this degree of neutralization is generally between 30 and 80% and preferably between 40 and 70% if the polymer has less than 2 meq/g of carboxylic acid functions, and between 10 and 50% and preferably between 10 and 40% if the polymer has more than 2 meq/g of carboxylic acid functions.

According to the invention, the neutralization of the carboxylic acid functions is carried out using a non-volatile monobasic agent chosen, for example, from an inorganic base such as sodium hydroxide or potassium hydroxide or from an amino alcohol selected from the group consisting of 2-amino-2-methyl-1-propanol (AMP), triethanolamine, triisopropanolamine (TIPA), monoethanolamine, diethanolamine, tris(2-hydroxy-1-propyl)amine, 2-amino-2-methyl-1,3-propanediol (AMPD) and 2-amino-2-hydroxymethyl-1,3-propanediol.

In the preparation of the pseudolatices used in the compositions according to the invention, the neutralization of the carboxylic acid functions of the film-forming polymer is carried out in situ in the solution of the polymer in the organic solvent, by adding the specified quantity of the non-volatile monobasic compound. The organic solvent used must be a volatile solvent or a mixture of such solvents possessing a boiling point below that of water, and must be miscible or partially miscible with water.

The organic solvent as defined above is preferably chosen from acetone, methyl ethyl ketone, tetrahydrofuran, methyl acetate, ethyl acetate, isopropanol and ethanol.

After the solution of the partially neutralized polymer in the organic solvent has been obtained, the preparation of an emulsion is then carried out by pouring a suitable quantity of water, optionally containing an antifoaming agent whose role will be to facilitate the subsequent evaporation of the organic phase, with stirring into the organic solution obtained.

According to a variant of the process as defined above, the neutralization of the carboxylic acid functions of the polymer dissolved in the organic solvent may be carried out during the formation of the emulsion by introducing an aqueous solution containing the requisite quantity of the non-volatile monobasic compound.

During the formation of the emulsion, the stirring is preferably carried out using a shearing disperser of the Moritz or Ultra-Turrax or Raineri type equipped with deflocculating blades.

The emulsion thereby obtained is especially stable without it being necessary to employ a surfactant in so far as the carboxylate groups of the polymer position themselves at the interface with water and protect the droplets from coalescence by electrostatic repulsion.

After formation of the emulsion at a temperature between room temperature and approximately 70° C., evaporation of the organic solvent is then carried out under reduced pressure until it has been completely removed, the evaporation preferably being carried out with gentle heating.

A pseudolatex, that is to say an aqueous dispersion of particles of the film-forming polymer, is thereby obtained, which pseudolatex is free from all surfactants or other hydrophilic stabilizers while being very stable, which is especially advantageous in hair-care cosmetics. In effect, the presence of a surfactant in an aerosol lacquer very often imparts adverse cosmetic properties to hair and a sensitivity to moisture uptake which manifests itself in an unpleasant sticky feel.

The average size of the particles is between 10 and 300 nm, but is preferably less than 250 nm.

The size polydispersity of the particles is relatively small according to this process for preparing the pseudolatex; measured in quasi-elastic light scattering, it is generally between 0.1 and 0.40 and preferably less than 0.35.

As is well known, plasticizing agents are generally liquid compounds with a high boiling point which enable the gloss transition temperature and also the softening temperature of polymers to be lowered, thereby endowing them with better flexibility.

The plasticizing agent is generally present in a proportion of between 0.1 and 80%, preferably between 5 and 40% and especially between 10 and 30% by weight relative to the weight of the neutralized film-forming polymer.

The plasticizing agent, which can be of the hydrophilic or hydrophobic type, is preferably introduced in the form of a mixture in the organic solvent during the preparation of the pseudolatex, and in particular when it is of the hydrophobic type.

When the plasticizing agent is of the hydrophilic type, it may be introduced into the dispersion after the formation of the pseudolatex.

Among plasticizing agents which may be used according to the invention, there may be mentioned:

the Carbitols of the company Union Carbide, namely Carbitol or diethylene glycol ethyl ether, methyl Carbitol or diethylene glycol methyl ether, butyl Carbitol or diethylene glycol butyl ether or alternatively hexyl Carbitol or diethylene glycol hexyl ether, the Cellosolves of the company Union Carbide, namely Cellosolve or ethylene glycol ethyl ether, butyl Cellosolve or ethylene glycol butyl ether or hexyl Cellosolve or ethylene glycol hexyl ether, propylene glycol derivatives, and especially propylene glycol phenyl ether, propylene glycol diacetate, dipropylene glycol butyl ether and tripropylene glycol butyl ether, as well as the Dowanols of the company Dow Chemical, namely Dowanol PM or propylene glycol methyl ether, Dowanol DPM or dipropylene glycol methyl ether and Dowanol TPM or tripropylene glycol methyl ether.

There may also be mention:

diethylene glycol methyl ether or Dowanol DM of the company Dow Chemical, oxyethylenated caster oil containing 40 mol of ethylene oxide, such as that sold by the company Rhône Poulenc under the name "Mulgofen EL-719", benzyl alcohol, triethyl citrate sold by the company Pfizer under the name "Citroflex-2, 1,3-burylone glycol, diethyl, dibutyl and diisopropyl phthalates and adipates, diethyl and dibutyl tartrates, diethyl, dibutyl and di(2-ethylhexyl) phosphates, and glycerol esters such as glyceryl diacetate (diacetin) and glyceryl triacetate (triacetin).

The plasticizing agent is preferably chosen from the group consisting of dipropylene glycol methyl ether, tripropylene glycol methyl ether, diethyl adipate and diisopropyl adipate.

The weight concentration of the film-forming polymer in the form of particles in the pseudolatex obtained by the process as described above is generally between 5 and 50% and preferably between 10 and 25% relative to the total weight of the pseudolatex.

The viscosity of the pseudolatices at a concentration of 25% by weight of particles of film-forming polymer should preferably be between 10 cP and 3,000 cP (measured in a Contraves instrument at 25° C.).

The cosmetic hair-care compositions for fixing the hair according to the invention take the form, as mentioned above, of an aerosol lacquer, a fixing lotion for manual spraying, a setting lotion or alternatively a styling mousse. The weight proportion of polymer in these compositions is between 1 and 40% relative to the total weight of the composition.

The use of a plasticized pseudolatex as defined above in the production of aerosol lacquers possesses a very large number of advantages in comparison to the usual aerosol lacquers in which the same polymers are used in the dissolved state in aqueous, aqueous-alcoholic or alcoholic solution.

The main advantage is that of being able to obtain water-based lacquers possessing all the desired cosmetic properties and a much faster drying time than the usual water-based lacquers as a result of the presence of a much smaller quantity of water.

Moreover, this drying time is also favoured in some cases by the fact that, by using a plasticized pseudolatex, the proportion of propellent agent relative to the aqueous phase containing the pseudolatex can be increased to an especially significant extent without segregation of constituents and appearance of a second liquid phase taking place.

This is most especially true, and it has been possible to demonstrate this, when the propellent agent is dimethyl ether, which is a partially water-miscible liquified gas.

With this propellent agent, it is possible in this way to obtain excellent aerosol lacquers containing a proportion of it which is greater than or equal to 40%.

In contrast, when the film-forming polymer is dissolved in the aqueous phase and no longer in the form of a pseudolatex, the proportion of propellent agent such as dimethyl ether must be maintained at a much lower level if it is desired to avoid a phase separation. This hence results in a relatively large aqueous phase, generally of more than approximately 65%, the outcome of which is a much longer drying time.

Although reference has been made above to the use of dimethyl ether as a propellent agent, it is self-evident that other propellent agents may be employed according to the invention for the production of the aerosol lacquers.

Among these, nitrogen, compressed air, carbon dioxide, hydrocarbons such as propane, butane and isobutane and fluorinated derivatives of aliphatic and cyclic hydrocarbons and in particular difluoroethanes, tetrafluoroethanes and octafluorocyclobutanes, may be mentioned in particular, it being possible for them to be used alone or mixed. It is preferable, according to the invention, to use dimethyl ether.

In the aerosol lacquers according to the invention, the plasticized pseudolatex is used in a proportion such that the dispersed film-forming polymer is present at a concentration of between 2 and 30% and preferably between 5 and 20% by weight relative to the total weight of the composition.

The total proportion of water is generally between 38 and 63% by weight and preferably between 45 and 60% relative to the total weight of the composition.

The proportion of propellent agent, when it is liquifiable, such as dimethyl ether, is generally between 20 and 60% and preferably between 30 and 55% so as to yield a single liquified phase within the aerosol container.

When the hair-care composition according to the invention takes the form of a fixing or setting lotion, the plasticized pseudolatex is generally present in a proportion such that the composition possesses a content of film-forming polymer of between 2 and 30% and preferably between 5 and 20%, the total water content being between 70 and 86% by weight relative to the total weight of the composition.

When the composition according to the invention takes the form of a styling mousse, the plasticized pseudolatex is generally present in a proportion such that the composition possesses a content of film-forming polymer of between 2 and 15% and preferably between 2 and 10%. The water content is preferably between 70 and 90% and that of the propellent agent between 2 and 15% by weight, it being possible for the propellent agent to be one of those that are mentioned above.

The cosmetic compositions for fixing the hair according to the invention can also contain various cosmetic additives such as sunscreen agents, polymers including the crosslinked homopolymer of methacryloyloxyethyltrimethylammonium chloride and crosslinked copolymers of acrylamide and a monomer chosen from neutralized 2-acrylamido-2-methylpropanesulphonic acid, ammonium acrylate and methacryloyloxyethyltrimethylammonium chloride, proteins, silicones, organo-modified or otherwise, volatile or otherwise, antifoaming agents, hydrating agents humectants, perfumes, preservatives, colorants, antioxidants, and the like.

Several examples of preparation of plasticized pseudolatex will now be given by way of illustration.

EXAMPLES OF PREPARATION OF THE PSEUDOLATICES

Example 1

Preparation of the vinyl acetate/crotonic acid polyoxyethylenated copolymer ("Aristoflex A" of the company Hoechst)-tripropylene glycol monomethyl ether plasticized pseudolatex.

50 g of "Aristoflex A" copolymer in powder form (measured acid value=65) are added gradually with stirring to a homogeneous solution of 186.9 g of methyl ethyl ketone, 3. 115 g of 2-amino-2-methyl-1-propanol (AMP) (quantity corresponding to 70% neutralization on the basis of the acid value of the "Aristoflex A" copolymer) and 10 g of tripropylene glycol monomethyl ether.

After stirring has been continued for 30 minutes, dissolution of the copolymer is complete.

To the organic phase thereby obtained, an aqueous phase is added with stirring using a Moritz disperser at 2,500 rpm to produce the emulsion, this aqueous phase consisting of 274.45 g of deionized water and 0.57 g of a silicone antifoaming agent "Burst RSD10.

The addition of the aqueous phase is carried out in the course of approximately 15 minutes, and stirring is then maintained at 3,000 rpm for 15 minutes. A moderately viscous emulsion of milky appearance is thereby obtained.

Evaporation of all of the organic solvent is then carried out using a rotary evaporator under partial vacuum and heating to approximately 40°–45° C. Evaporation is continued until the methyl ethyl ketone has been completely removed in conformity with the azeotropic mixture formed with water.

The quantity of water removed by formation of the azeotropic mixture is then added back to the dispersion to obtain a plasticized pseudolatex having a concentration of film-forming polymer of 15% and of plasticizing agent of 3%. The plasticized pseudolatex obtained is stable, slightly blueish and opaque in appearance and moderately viscous.

The particle size was measured in quasi-elastic light scattering using a Coulter model M4 instrument, and gave the following results:

average particle size: 207 nm polydispersity factor=0.11

According to the same procedure as that described above, plasticized pseudolatices were also prepared using the commercial copolymers "Luviset CA 66", "Amphomer LV 71", "Gantrez ES425" and "Resin 28-29-30" containing tripropylene glycol monomethyl ether or diisopropyl adipate as plasticizing agent.

The production conditions and characteristics of the plasticized pseudolatices obtained are given in Table I below.

produce the emulsion, this aqueous phase consisting of 265.55 g of deionized water and 1.14 g of a silicone antifoaming agent (Burst RSD 10).

After the addition of the aqueous phase at room temperature is complete, stirring is continued for 10 to 15 min, making it possible to lead to the production of a translucent and stable emulsion.

Concentration is then carried out using a rotary evaporator under partial vacuum at a temperature below 45° C. After the acetone has been completely removed, a milky stable dispersion of low viscosity is obtained.

The concentration of film-forming polymer is 25%, and that of plasticizing agent 5%.

The particle size was measured in quasi-elastic light scattering, using a Coulter model M4 instrument, and gave the following results:

TABLE I

| Pseudolatex | EX. 2 | EX. 3 | EX. 4 | EX. 5 | EX. 6 |
|---|---|---|---|---|---|
| Films-forming polymer (acid value = $I_a$) | LUVISET CA66 $I_a = 74$ | AMPHOMER $I_a = 137$ | GANTRE % E6425 $I_a = 260$ | RESIN 28-29-30 $I_a = 65$ | RESIN 28-29-30 $I_a = 65$ |
| Neutralizing agent | AMP | AMP | AMP | AMP | AMP |
| Degree of neutralization | 50% | 30% | 10% | 50% | 5% |
| ORGANIC PHASE | | | | | |
| Quantity of polymer | 60 g | 150 g | 12 g | 60 g | 60 g |
| Quantity of neutralizing agent | 3.5 g | 9.80 g | 0.451 g | 3 g | 3 g |
| Plasticizing agent | Tripropylene glycol monomethyl ether 12 g | Tripropylene glycol monomethyl ether 30 g | Tripropylene glycol monomethyl ether 2.4 g | Tripropylene glycol monomethyl ether 12 g | Diisopropyl adipate 12 g |
| Volatile organic solvent | Methyl ethyl ketone 225 g | Tetrahydrofuran 1063 g | Methyl ethyl ketone 45.15 g | Methyl ethyl ketone 225 g | Methyl ethyl ketone 231 g |
| AQUEOUS PHASE | | | | | |
| Silicone anitfoam | 0.69 g | 1.71 g | 0.137 g | 0.69 g | 0.69 g |
| Deionized water | 325 g | 812 g | 59.86 g | 325 g | 331 g |
| Emulsion formation temperature | Room temperature | Room temperature | Room temperature | 60° C. | 60° C. |
| Polymer concentration in the pseudolatex | 15% | 15% | 20% | 15% | 15% |
| Plasticizing agent concentration in the pseudolatex | 3% | 3% | 4% | 3% | 3% |
| Average particle diameter | 247 nm | 299 nm | 206 nm | 148 nm | 200 nm |
| Size polydispersity of the particles | 0.47 | 0.33 | 0.11 | 0.15 | 0.28 |
| Surface energy of the film | | | | 35 mJ/m$^2$ | 30 mJ/m$^2$ |
| Polarity | | | | 0 | 0 |

Example 7

Preparation of the vinyl acetate/crotonic acid/vinyl 4-tert-butylbenzoate (6'5:10:25) copolymer-diethyl adipate plasticized pseudolatex.

The preparation of this copolymer is described in Example 19 of French Patent No. 78/30,596 (No. 2,439,798) and it takes the form of beads from 0.5 to 1 mm in diameter.

100 g of the copolymer defined above (acid value: 65) are added gradually with stirring to a homogeneous solution of 280 g of acetone, 6.2 g of 2-amino-2-methyl-1-propanol (quantity corresponding to 50% neutralization on the basis of the acid value) and 20 g of diethyl adipate.

After stirring at room temperature for 30 minutes, dissolution of the polymer is complete.

To the organic phase thereby obtained, an aqueous phase is added with stirring in the course of 5 minutes using a shearing disperser of the Ultra-Turrax type at 2,000 rpm to Average particle size: 161 nm Polydispersity factor: 0.25

The characteristics of the film obtained after drying the plasticized pseudolatex are:

Surface energy: 42 mJ/m$^2$

Polarity: 0.29

According to the same procedure as that described above, other plasticized pseudolatices were also prepared from the same polymer of Example 19 of French Patent No. 78/30, 596 (No. 2,439,798), but varying the degree of neutralization and deploying other neutralizing agents.

The characteristics of the plasticized pseudolatices obtained, together with the production conditions, are given in Table II below.

TABLE II

| Pseudolatex | EX. 8 | EX. 9 | EX. 10 | EX. 11 | EX. 12 | EX. 13 |
|---|---|---|---|---|---|---|
| Film-forming polymer | " Ex. 7 | " Ex. 7 | " Ex. 7 | " Ex. 7 | " Ex. 7 | " Ex. 7 |
| Neutralizing agent | AMP | Triethanolamine | TIPA | NaOH | KOH | AMP |
| Degree of neutralization | 70% | 70% | 60% | 60% | 70% | 60% |
| ORGANIC PHASE | | | | | | |
| Quantity of polymer | 30 g | 40 g | 40 g | 40 g | 30 g | 100 g |
| Quantity of neutralizing agent | 2.17 g | 4.85 g | 5.32 g | / | / | / |
| Plasticizing agent | Diethyl adipate | Diisopropyl adipate | Diisopropyl adipate | Diethyl adipate | Diethyl adipate | Diisopropyl adipate |
| | 6 g | 10 g | 8 g | 10 g | 6 g | 25 g |
| Volatile organic solvent | Acetone | Acetone | Acetone | Acetone | Acetone | Acetone |
| | 81.83 g | 105.14 g | 106.7 g | 109 g | 83 g | 275 g |
| AQUEOUS PHASE | | | | | | |
| Silicone antifoam | 0.34 g | 0.45 g | 0.45 g | 0.45 g | 0.45 g | 1.14 g |
| Quantity of neutralizing agent | / | / | / | 5.58 ml (5 N) | 4.88 ml (5 N) | 6.2 g |
| Deionized water | 81.49 g | 104.68 g | 106.2 g | 104 g | 78.66 g | 260.55 g |
| Emulsion formation temperature | Room temperature | Room temperature | Room temperature | Room temperature | Room temperature | Room temperature |
| Polymer concentration in the pseudolatex | 25% | 25% | 25% | 25% | 25% | 25% |
| Plasticizing agent concentration in the pseudolatex | 5% | 6.25% | 5% | 6.25% | 5% | 6.25% |
| Average particle diameter | 80 nm | 90 nm | 188 nm | 60 nm | 100 nm | 58 nm |
| Size polydispersity of the particles | 0.22 | 0.32 | 0.4 | 0.25 | 0.35 | 0.3 |
| Surface energy of the film | | | | | | 50 mJ/m$^2$ |
| Polarity | | | | | | 0.24 |

Various plasticized pseudolatices were also prepared from other film-forming polymers described in French Patent No. 78/30,596.

The polymers used were as follows:

Polymer A

Vinyl acetate/crotonic acid/vinyl 4-tert-butyl-benzoate/vinyl neodecanoate (57:10:25:8) polymer.

Polymer B

Vinyl acetate/crotonic acid/vinyl 4-tert-butyl-benzoate/vinyl neodecanoate (70:10:10:10) polymer.

Polymer C

Vinyl acetate/crotonic acid/vinyl benzoate/vinyl neodecanoate (70:10:10:10) polymer.

Polymer D

Vinyl acetate/crotonic acid/vinyl 4-tert-butyl-benzoate/allyl stearate (70:10:10:10) polymer.

From the film-forming polymers A to D, plasticized pseudolatices were prepared according to the same procedure as that described in Example 7. The production conditions and characteristics of the plasticized pseudolatices obtained are given below in Table III.

TABLE III

| Pseudolatex | EX. 14 | EX. 15 | EX. 16 | EX. 17 | EX. 18 |
|---|---|---|---|---|---|
| Film-forming polymer (acid value = $I_a$) | Polymer A $I_a = 65$ | Polymer B $I_a = 65$ | Polymer C $I_a = 65$ | Polymer D $I_a = 65$ | Polymer D $I_a = 65$ |
| Neutralizing agent | AMP | AMP | AMP | AMP | AMP |
| Degree of neutralization | 50% | 50% | 55% | 40% | 50% |
| ORGANIC PHASE | | | | | |
| Quantity of polymer | 17.5 g | 17.5 g | 12.65 g | 17.5 g | 17.5 g |
| Quantity of neutralizing agent | 0.9 g | 0.9 g | 0.72 g | 0.72 g | 0.9 g |
| Plasticizing agent | Diethyl adipate | Diethyl adipate | Diethyl adipate | Diethyl adipate | Diethyl adipate |
| | 3.5 g | 3.5 g | 2.53 g | 3.5 g | 3.5 g |
| Volatile organic solvent | Acetone | Acetone | Acetone | Acetone | Acetone |
| | 48.1 g | 48.1 g | 34.7 g | 48.3 g | 48.1 g |
| AQUEOUS PHASE | | | | | |
| Silicone antifoam | 0.2 g | 0.2 g | 0.14 g | 0.2 g | 0.2 g |
| Deionized water | 47.9 g | 47.9 g | 34.5 g | 48.1 g | 47.9 g |
| Emulsion formation temperature | Room temperature | Room temperature | Room temperature | Room temperature | Room temperature |
| Polymer concentration in the pseudolatex | 25% | 25% | 25% | 25% | 25% |
| Plasticizing agent concentration in the pseudolatex | 5% | 5% | 5% | 5% | 5% |
| Average particle diameter | 120 nm | 90 nm | 100 nm | 110 nm | 90 nm |
| Size polydispersity of the particles | 0.4 | 0.3 | 0.36 | 0.17 | 0.27 |

Example 19

Preparation of the vinyl acetate/crotonic acid/vinyl neodecanoate terpolymer ("Resin 28-29-30" of the company National Starch)-tripropylene glycol monomethyl ether plasticized pseudolatex.

60 g of "Resin 28–29–30" terpolymer in powder form are added with stirring to a solution of 225 g of methyl ethyl ketone and 3 g of 2-amino-2-methyl-1-propanol (quantity corresponding to 50% neutralization on the basis of the acid value of the "Resin 28–29–30" terpolymer).

After stirring has been continued for 30minutes, dissolution of the copolymer is complete.

To the organic phase thereby obtained, an aqueous phase is added with stirring using a Moritz disperser at 2,500 rpm to produce the emulsion, this aqueous phase consisting of 325 g of deionized water and 0.69 g of silicone antifoaming agent "Burst RSD10".

The addition of the aqueous phase is carried out in the course of approximately 15 minutes, and stirring is then maintained at 3,000 rpm for 15 minutes. A moderately viscous emulsion of milky appearance is thereby obtained.

Evaporation of all of the organic solvent is then carried out using a rotary evaporator under partial vacuum and heating to approximately 40°–45° C. Evaporation is continued until the methyl ethyl ketone has been completely removed in conformity with the azeotropic mixture formed with water.

The quantity of water removed by formation of the azeotropic mixture is then added back to the dispersion to obtain a pseudolatex having a concentration of film-forming polymer of 15.4%.

To the dispersion obtained, 12 g of tripropylene glycol monomethyl ether, a quantity corresponding to 20% by weight of plasticizer relative to the weight of unneutralized polymer, are added with stirring. The mixture is left stirring for 48 hours at room temperature. The plasticized pseudolatex thereby obtained is stable and contains 15% of polymer and 3% of plasticizer.

The particle size was measured in quasi-elastic light scattering using a Coulter model M4 instrument, and gave the following results:

Average particle size: 140 nm

Polydispersity factor: 0.20

The characteristics of this plasticized pseudolatex are very similar to those of the plasticized pseudolatex obtained according to the process of Example 5, in which the plasticizing agent is introduced in the form of a mixture in the organic solvent.

FORMULATION EXAMPLES

Example A:

An aerosol hair lacquer is prepared by packaging, in a suitable aerosol container:

| | |
|---|---|
| Plasticized pseudolatex of Example 7 | 52 g |
| Dimethyl ether | 45 g |
| Perfume | 0.05 g |
| Water q.s. | 100 g |

The mixture forms just a single phase.

The valve is attached and the container is hermetically sealed.

The lacquer applied to the hair does not present a whitish appearance, and it dries quickly, possesses good lacquering power and good hold and does not produce a sticky effect on application and after drying.

The polymer film is removed readily on shampooing.

Example B:

According to the same procedure as that described in Example A, an aerosol hair lacquer having the following composition was prepared:

| | |
|---|---|
| Plasticized pseudolatex of Example 10 | 36 g |
| Dimethyl ether | 48 g |
| Perfume | 0.05 g |
| Water q.s. | 100 g |

The mixture takes the form of a single homogeneous phase.

After spraying, drying is fast and an excellent hold of the hair is obtained.

The lacquer is removed readily on shampooing.

Example C:

According to the same procedure as that described in Example A, an aerosol hair lacquer having the following composition was prepared:

| | |
|---|---|
| Plasticized pseudolatex of Example 18 | 40 g |
| Perfume, colorant Preservative q.s. | |
| Dimethyl ether | 50 g |
| Water q.s. | 100 g |

The mixture takes the form of a single homogeneous phase.

Example D:

According to the same procedure as that described in Example A, an aerosol hair lacquer having the following composition was prepared:

| | |
|---|---|
| Plasticized pseudolatex of Example 14 | 24 g |
| Perfume, colorant, preservative q.s. | |
| Dimethyl ether | 30 g |
| Water q.s. | 100 g |

Example E:

A fixing spray in a pump bottle is prepared by packaging, in a suitable container:

| | |
|---|---|
| Plasticized pseudolatex of Example 16 | 32 g |
| Perfume, colorant, preservative q.s. | |
| Water q.s. | 100 g |

The container when filled is then equipped with a spraying pump.

Example F:

A fixing spray is prepared by making the following mixture:

| | |
|---|---|
| Plasticized pseudolatex of Example 15 | 60 g |
| Perfume, colorant, preservative q.s. | |
| Water q.s. | 100 g |

The lotion obtained is then packaged in an atomizer which is rechargeable with compressed air.

Example G:

A setting lotion having the following composition is prepared:

| | |
|---|---|
| Plasticized pseudolatex of Example 15 | 40 g |
| Perfume, colorant preservative q.s. | |
| Water q.s. | 100 g |

Example H:

An aerosol styling mousse having the following composition is prepared:

| | |
|---|---|
| Plasticized pseudolatex of Example 7 | 4 g |
| Polyvinyl alcohol sold under the name "Mowiol 4088" by the company Hoechst | 0.5 g |
| Perfume, colorant, preservative q.s. | |
| Water q.s. | 100 g |

90 g of the composition obtained are introduced into an aerosol can without a dip tube. The valve is attached and the container is hermetically sealed, and 10 g of a butane/isobutane/propane propellent mixture (3.2 bars) are then introduced.

Example I:

According to the same procedure as that in Example A, an aerosol hair lacquer having the following composition was prepared:

| | |
|---|---|
| Plasticized pseudolatex of Example 15 | 28 g |
| Perfume, colorant, preservative q.s. | |
| Dimethyl ether | 30 g |
| Water q.s. | 100 g |

The mixture takes the form of a single homogeneous phase.

The lacquer applied to the hair possesses a short drying time and good lacquering power.

The film is readily removed on brushing and shampooing.

Example J:

According to the same procedure as that described in Example H, a styling mousse having the following composition was prepared:

| | |
|---|---|
| Plasticized pseudolatex of Example 7 | 40 g |
| Hydroxyethylcellulose cetyl ester sold under the name "Natrosol Plus 330 CS" by the company Aqualon | 0.5 g |
| Perfume, colorant, preservative q.s. | |
| Demineralized water q.s. | 100 g |

90 g of the composition thereby obtained are introduced into an aerosol can without a dip tube. The valve is attached and the container is hermetically sealed. 10 g of a butane/isobutane/propane propellent mixture (3.2 bars) are then introduced.

On spraying, a rigid and firm mousse is obtained, which provides fixing power as well as good cosmetic properties, in particular a good sheen.

Example K:

According to the same procedure as that described in Example A, an aerosol hair lacquer having the following composition was prepared:

| | |
|---|---|
| Plasticized pseudolatex of Example 5 | 59.4 g |
| Dimethyl ether | 40 g |
| Perfume, colorant, preservative q.s. | |
| Demineralized water q.s. | 100 g |

Example L:

According to the same procedure as that described in Example A, an aerosol hair lacquer having the following composition was prepared:

| | |
|---|---|
| Plasticized pseudolatex of Example 4 | 25 g |
| Dimethyl ether | 30 g |
| Perfume, colorant, preservative q.s. | |
| Demineralized water q.s. | 100 g |

Example M:

According to the same procedure as that described in Example E, a fixing spray in a pump bottle having the following composition was prepared:

| | |
|---|---|
| Plasticized pseudolatex of Example 1 | 33.3 g |
| Perfume, colorant, preservative q.s. | |
| Demineralized water q.s. | 100 g |

Example N:

According to the same procedure as that described in Example F, a fixing spray having the following composition, packaged in an atomizer which is rechargeable with compressed air, was prepared:

| | |
|---|---|
| Plasticized pseudolatex of Example 2 | 46.7 g |
| Perfume, colorant, preservative q.s. | |
| Demineralized water q.s. | 100 g |

Example O:

A setting lotion having the following composition is prepared:

| | |
|---|---|
| Plasticized pseudolatex of Example 4 | 20 g |
| Perfume, colorant, preservative q.s. | |
| Demineralized water q.s. | 100 g |

Example P:

An aerosol styling mousse having the following composition is prepared:

| | |
|---|---|
| Plasticized pseudolatex of Example 4 | 15 g |
| Polyvinyl alcohol sold under the name "Mowiol 4088" by the | 0.5 g |

| | |
|---|---|
| company Hoechst | |
| Perfume, colorant, preservative q.s. | |
| Water q.s. | 100 g |

90 g of the composition obtained are introduced into an aerosol can without a dip tube. The valve is attached and the container is hermetically sealed, and 10 g of a butane/propane/isobutane propellent mixture (3.2 bars) are then introduced.

Example Q:

According to the same procedure as that in Example A, an aerosol hair lacquer having the following composition was prepared:

| | |
|---|---|
| Plasticized pseudolatex of Example 15 | 32 g |
| Perfume, colorant, preservative q.s | |
| Dimethyl ether | 40 g |
| Water q.s. | 100 g |

The mixture takes the form of a single homogeneous phase.

Example R:

According to the same procedure as that in Example A, an aerosol hair lacquer having the following composition was prepared:

| | |
|---|---|
| Plasticized pseudolatex of Example 7 | 35.6 g |
| Dimethicone copolyol sold under the name "Silbione Huile 70646" by the company Rhone Poulenc | 0.5 g |
| Perfume q.s. | |
| Dimethyl ether | 40 g |
| Water q.s. | 100 g |

The mixture takes the form of a single phase. Good spraying, good fixing qualities, good cosmetic qualities, good disentangling on brushing and good removal on shampooing are obtained.

We claim:

1. A process for fixing hair comprising applying to the hair a sufficient amount of aerosol hair lacquer for fixing said hair, said aerosol hair lacquer being in the form of a single homogeneous phase and comprising:
   (1) an aqueous dispersion of:
      (a) particles of a water-insoluble film-forming polymer containing carboxylic acid functions having an average diameter of between 10 and 300 nm, said film-forming polymer being selected from the group consisting of:
         (i) vinyl acetate/crotonic acid polyoxy-ethylentated copolymers,
         (ii) vinyl acetate/crotoncic acid copolymers,
         (iii) vinyl acetate/crotoncic acid/vinyl neodecanoate terpolymers,
         (iv) N-octylacrylamide/methylmeth-acrylate/hydroxypropyl methacrylate/acrylic acid/tertbutyl-aminoethyl methacrylate copolymers,
         (v) methyl vinyl ether/maleic anhydride alternating copolymers monesterified with butanol,
         (vi) acrylic acid/ethyl acrylate/N-tert-butyl-acrylamide terpolymers, and
         (vii) polymers corresponding to the following formula:

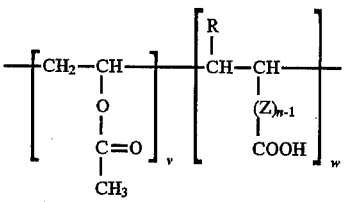

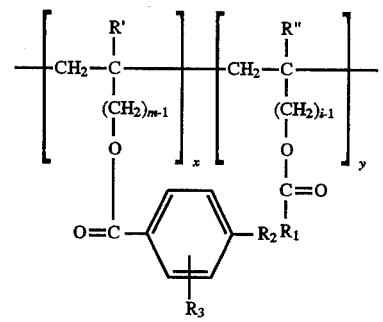

in which:

R, R' and R" which may be identical or different, represent a hydrogen atom or a methyl radical;

m, n and t are 1 or 2;

$R_1$ represents a saturated or unsaturated, linear or branched alkyl radical having from 2 to 21 carbon atoms;

$R_2$ represents a hydrogen atom, a methyl, ethyl, tertbutyl, ethoxy, butoxy or dodecyloxy radical;

$R_3$ represents a hydrogen atom, an alkyl radical having 1 to 4 carbon atoms or an alkoxy radical having 1 to 4 carbon atoms;

z represents a bivalent radical selected from the group consisting of: $-CH_2-$, $-CH_2-O-CH_2-$ and $-CH_2-O-(CH_2)_2-$;

v represents from 10 to 91% by weight of said polymer;

w represents from 3 to 20% by weight of said polymer;

x represents 4 to 60% by weight of said polymer; and y represents from 0 to 40% by weight of said polymer;

v+w+x+y being equal to 100% by weight of said polymer; the carboxylic acid functions of said film-forming polymer being neutralized with a non-volatile monobasic agent to a degree of neutralization of between 30 and 80% if the film-forming polymer has less than 2 meq/g of carboxylic acid functions and of between 10 and 50% if the polymer has more than 2 meq/g of carboxylic acid functions; and (b) a plasticizing agent, present between 0.1 to 80% by weight relative to the weight of the neutralized film-forming polymer, said agent being distributed according to said agent's partition coefficient between said particles and the aqueous phase, said particles of the dispersed film-forming polymer being present between 2 and 30% by weight relative to the total weight of the composition;

(2) water in a proportion in which the total water content is between 38 and 90% by weight relative to the total weight of the composition; and (3) a propellant in a proportion between 20 and 60% by weight relative to the total weight of the aerosol hair lacquer.

2. A process for fixing hair comprising applying to the hair a sufficient amount of an aqueous composition for fixing said hair, said composition containing:
   (1) an aqueous dispersion of:
      (a) particles of a water-insoluble film-forming polymer containing carboxylic acid functions having an average diameter of between 10 and 300nm, said film-forming polymer being selected from the group consisting of:
(i) vinyl acetate/crotonic acid polyoxyethylenated copolymers,
(ii) vinyl acetate/crotonic acid copolymers,
(iii) vinyl acetate/crotonic acid/vinyl neodecanoate terpolymers,
(iv) N-octylacrylamide/methyl meth-acrylate/hydroxypropyl methacrylate/acrylic acid/tert-butylaminoethyl methacrylate copolymers,
(v) methyl vinyl ether/maleic anhydride alternating copolymers monoesterified with butanol,
(vi) acrylic acid/ethyl acrylate/N-tert-butyl-acrylamide terpolymers, and
(vii) polymers corresponding to the following formula:

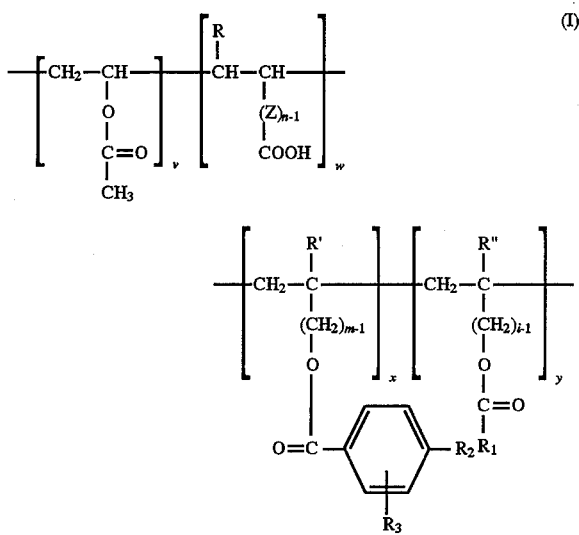

in which:
R, R' and R" which may be identical or different, represent a hydrogen atom or a methyl radical;
m, n and t are 1 or 2;
$R_1$ represents a saturated or unsaturated, linear or branched alkyl radical having from 2 to 21 carbon atoms;
$R_2$ represents a hydrogen atom, a methyl, ethyl, tert-butyl, ethoxy, butoxy or dodecyloxy radical;
$R_3$ represents a hydrogen atom, an alkyl radical having 1 to 4 carbon atoms or an alkoxy radical having 1 to 4 carbon atoms;
z represents a bivalent radical selected from the group consisting of: —$CH_2$—, —$CH_2$—O—$CH_2$— and —$CH_2$—O—$(CH_2)_2$—;
v represents from 10 to 91% by weight of said polymer;
w represents from 3 to 20% by weight of said polymer;
x represents from 4 to 60% by weight of said polymer; and
y represents from 0 to 40% by weight of said polymer;
v+w+x+y being equal to 100% by weight of said polymer;
the carboxylic acid functions of said film-forming polymer being neutralized with a non-volatile monobasic agent to a degree of neutralization of between 30 and 80% if the film-forming polymer has less than 2 meq/g of carboxylic acid functions and of between 10 and 50% if the polymer has more than 2 meq/g of carboxylic acid functions; and (b) a plasticizing agent, present between 0.1 to 80% by weight relative to the weight of the neutralized film-forming polymer, said agent being distributed according to said agent's partition coefficient between said particles and the aqueous phase, said particles of the dispersed film-forming polymer being present between 2 and 30% by weight relative to the total weight of the composition; and (2) a vehicle consisting of water in a proportion in which the total water content is between 38 and 90% by weight relative to the total weight of the composition.

3. The process according to claim 2, wherein said aqueous composition contains said water in a proportion in which the total water content is between 70 and 86% by weight relative to the total weight of the composition.

4. The process according to claim 1, wherein said aqueous composition contains said water in a proportion in which the total water content is between 38 and 63% by weight and the propellant present in a proportion between 20 and 60% by weight relative to the total weight of the composition.

5. The process according to claim 1, wherein said propellant is dimethylether.

6. The process according to claim 1, wherein said aqueous composition contains said particles of the dispersed film-forming polymer in a portion between 2 and 15% by weight, said water in a proportion in which the total content is between 70 and 90% by weight and said propellant in a proportion between 2 and 15% by weight relative to the total weight of the composition.

7. The process according to claim 2, wherein said aqueous composition further contains a cosmetic ingredient selected from the group consisting of a sunscreen agent, an antifoaming agent, a hydrating agent, a humectant, a perfume, a preservative, a colorant, an antioxidant, a protein and a silicone.

* * * * *